(12) United States Patent
Knebel et al.

(10) Patent No.: US 7,934,323 B2
(45) Date of Patent: May 3, 2011

(54) METHOD AND A DEVICE FOR THE POSITIONING OF A DISPLACEABLE COMPONENT IN AN EXAMINING SYSTEM

(75) Inventors: Detlef Knebel, Berlin (DE); Torsten Jähnke, Lychen (DE)

(73) Assignee: JPK Instruments AG, Berlin (DE)

( * ) Notice: Subject to any disclaimer, the term of this patent is extended or adjusted under 35 U.S.C. 154(b) by 432 days.

(21) Appl. No.: 11/992,850

(22) PCT Filed: Sep. 29, 2006

(86) PCT No.: PCT/DE2006/001722
§ 371 (c)(1),
(2), (4) Date: Sep. 25, 2008

(87) PCT Pub. No.: WO2007/036222
PCT Pub. Date: Apr. 5, 2007

(65) Prior Publication Data
US 2009/0140685 A1 Jun. 4, 2009

(30) Foreign Application Priority Data

Sep. 29, 2005 (DE) .......................... 10 2005 047 729

(51) Int. Cl.
*G01B 5/00* (2006.01)
(52) U.S. Cl. ................. 33/559; 33/503; 33/556
(58) Field of Classification Search ........... 33/559, 33/503, 1 M, 556, 561, DIG. 2
See application file for complete search history.

(56) References Cited

U.S. PATENT DOCUMENTS

| 5,357,684 A | 10/1994 | Lindner et al. |
| 5,979,070 A | 11/1999 | Lau |
| 6,291,822 B1 | 9/2001 | Umemoto et al. |
| 6,788,220 B2 * | 9/2004 | Netzer .............................. 33/1 N |
| 7,395,698 B2 * | 7/2008 | Degertekin ..................... 33/561 |
| 2004/0168506 A1 * | 9/2004 | Knebel et al. ................. 73/61.44 |

FOREIGN PATENT DOCUMENTS

| DE | 42 04 632 A | 8/1993 |
| EP | 0 935 137 A | 8/1999 |

* cited by examiner

*Primary Examiner* — Yaritza Guadalupe-McCall
(74) *Attorney, Agent, or Firm* — Smith Patent Office

(57) ABSTRACT

The invention relates to a method and a device for the positioning of a displaceable component in an examining system, particularly a measuring or an analytic system wherein, during the process, the displaceable component is displaced with the support of an actuating element coupled to the displaceable component from a home position into an end position, wherein the actuating element is moved by means of a drive force and the displaceable component is impacted with a fixation force fixating the displaceable component in the end position by way of a fixation component connected to the displaceable component, where the fixation component is submerged at least partially in a reservoir of a medium and is fixated in the medium by means of the transformation of the medium from a liquid state into a solidified state, wherein the medium is transformed from the liquid state into the solidified state by means of the impact-application with a manipulating variable.

21 Claims, 3 Drawing Sheets

Figure 1A:
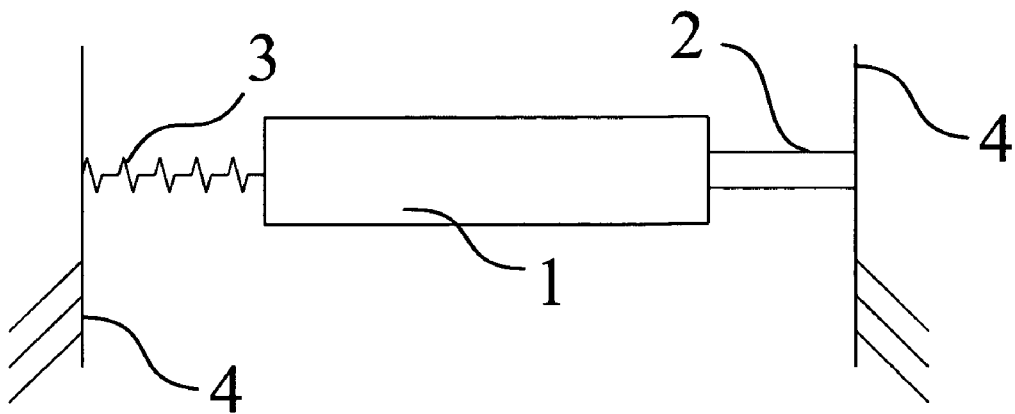

METHOD AND A DEVICE FOR THE POSITIONING OF A DISPLACEABLE COMPONENT IN AN EXAMINING SYSTEM

The invention relates to a method and a device for the positioning of a displaceable component in an examining system, particularly a measuring or an analytic system.

BACKGROUND OF THE INVENTION

The positioning of components is normally performed with the support of a setting element which serves the purpose of establishing a movement of a displaceable component opposite another component which, on its part, remains in the rest position during the displacement. In an examining system, the non-moved component during the displacement of the displaceable component can also be regarded as being a type of frame. For this reason, this designation is also adopted in the following.

The examining system in the sense of this application is a plant, an apparatus or a device that is suitable for performing research or analysis on any examination object with regard to at least one characteristic of a physical, chemical or biological nature. Such systems are frequently allocated to the field of the so-called scientific equipment construction. They are at least partly characterised by high-precision mechanical components, particularly where the exact displacement of displacement-capable components is concerned.

For setting elements which are required to function with a high-sensitivity resolution, piezo-electrically operated setting elements for example, which are also designated as piezoelements, are used as actuators whose expansion depends on an applied electric voltage. However, other setting elements are also known as such in the state of the art, for example hydraulically or inductively operated setting elements. With the known piezoelements, an actuating element actually causing a displacement of a component is, for example, moved to a pre-specified location by the setting of a voltage and remains solidly at that location. As piezo-elements have a hysteresis, meaning, the expansion at a certain voltage depends on the home position of the displacement motion and, beyond this, move for some time after the voltage has been switched off, also designated as "creeping", the actual deflection of the piezoelement or the displaceable component is to be measured during the operation of the piezoelement with a voltage activation and, with the support of a closed loop regulation, it must be ensured that the expansion of the piezoelement is effected linearly to the applied voltage. The quality of the linearity in this case naturally depends on the type of the selected spacing sensor which can be, for example, a capacitive sensor, an LVDT (linear variable differential transformer) or a strain gauge. However, other spacing sensors are useable such as for example optical sensors. Errors occur regularly with known types where corrections are performed with software controls.

The component to be displaced can either be solidly joined to the actuating element, by means of adhesive sticking for example, or a joint is formed with which the displaceable component is joined to the other component which remains locally fixed-positioned during the displacement action. A solid body joint is used, for example. In this case, piezoelements can be clamped in between the parts of the solid body joint or can be fastened to this in another way in order to initiate the displacement movement by means of a projection or a retraction of the joint.

In addition to this, a step-up mechanism is frequently used in order to convert the drive movement produced by a drive apparatus of the setting element for the displacement of the displaceable component. Thus, displacement routes are obtained which are larger than the extent or a stroke of the drive movement itself.

In the sense of the present application, a direct drive for the displacement movement is involved if the displacement of the displaceable component is achieved from a home position into an end position wherein an actuating element coupled to the displaceable component is moved between a retracted position in which the actuating element is at least partially retracted and a projected position in which the actuating element is at least partially projected. Such a direct drive can, for example, be provided for with the support of the piezoelement.

In contrast to this, indirect drives are also known. This includes, for example, the displacement of the displaceable component wherein a setting element provided with a thread is coupled to the displaceable component and is displaced by the turning of a screw in the thread. In this way, the setting element is moved longitudinally along the screw. However, such indirect connections normally lead to reduced dynamic effects and increased inaccuracy of the positioning.

The usage of a direct drive of the known type, however, also leads to disadvantageous effects. The process of the actuating element as required for the position finding must be upheld in the end position. For a piezoelement this means that, because of the coasting after the shutoff of the voltage (creeping) the applied voltage still has to be varied. The deflection of the actuating element additionally involves a noise. For example, a piezoelement requires a voltage source whose noise can be minimised but can never be fully suppressed. This noise causes a fluctuation of the position of the displaceable component in the end position by a required value (setpoint). If the end position is additionally monitored with the support of a sensor whose signals are used for a control, the resolution of the sensor can also represent a limitation of the positioning accuracy.

Moreover, and by way of a vibration-capable system to which the actuating element also belongs, the component to be displaced remains joined to the frame in the end position also. If the component to be displaced is, for example, adhesively joined to the actuating element or fastened to it directly in any form, the actuating element is itself a spring-mass-system. If disturbing movements are then imposed onto the overall system, this will then lead to problems if the spectrum of these disturbances lies in the vicinity of or above a resonance frequency of the overall system. In this situation, relative movements of the components to one another then occur.

The problems as described occur particularly with measurement and analytic equipment, such as with a scanning probe microscope, for example. In this case, both the resolution and the dynamics of the microscope are limited. Setting elements are normally used for all three spatial directions in such a microscope. The inaccuracy of the setting elements due to the noise sources restricts the measuring possibilities. With a lateral scanning range of 100 μm×100 μm, for example, an atomic resolution is often not possible because the voltage sources of the piezoelements generate noise. In the case of a control, the noise of the sensor adopted for the spacing measurement is added to the control signal. Accordingly, the setting element has a certain local blurring which amounts to approximately 0.3 nm for the previously mentioned example. The dynamics are determined by the size of required piezoelements or a correspondingly selected step-up, so that the speed cannot be randomly increased for any desirable scanning range. If a higher resolution or a higher bandwidth is desired, the scanning range must then be reduced.

SUMMARY OF THE INVENTION

The object of the invention is to provide for a method and a device for the positioning of a displaceable component in an examining system where the accuracy of the fixation of the displaceable component in the end position is improved.

This object is solved according to the invention by means of a method for the positioning of a displaceable component in an examining system according to the independent Claim 1 and a device for the positioning of a displaceable component in an examining system according to the independent Claim 11.

The invention comprises the conceptual idea of fixating a displaceable component in an end position in which it has gained access by means of the movement of an actuating element coupled to the displaceable component, which also can be designated as securing or fixation, wherein a fixation component connected to the displaceable component is fixated in a reservoir of a medium, in which the fixation component is at least partially immersed, which is achieved in that the medium from a liquid state is transformed into a solidified state. The solidified state compared to the liquid state is to be described in greater detail, for example, in that the medium has an increased viscosity opposite the liquid state, or is even characterised by solid body properties. In this manner and by way of the fixation component, a fixation force is initiated onto the displaceable component in the end position. The displaceable component is then fixed-positioned in a rest setting in the end position relative to the reservoir of the medium. If the vessel in which the reservoir of the medium is formed is in the resting status to another reference system, where this can be for example a device frame or another component in the case of an examining system, the displaceable component will also be kept in the resting status in the end position relative to the reference system. Disturbing influences on the displaceable component in the end position which can lead to a situation where the displaceable component moves out of the end position in an undesirable manner, are subdued or even completely suppressed.

The securing of the resting status of the displaceable component in the end position in the proposed mode enables the maintaining of the positioning of the displaceable component in the end position with high precision. Such a level of precision is, for example, desirable in conjunction with various experimental examinations. For example, in this way an improved force-spacing-spectroscopy is made possible because disturbing movements of the displaceable component are prevented.

A preferred further development of the invention envisages that, as a medium, a medium of at least one material type correspondingly selected from the following group of material types is adopted: rheological material such as electro-rheological material or magnetic-rheological material and Bingham-body. The Bingham-body here is a medium which is a non-newton liquid and begins to flow only when the yield strength is exceeded, meaning, a certain shear stress. Examples for non-newton media are brines, gels, suspensions with a higher concentration, synthetic materials, solutions or melts of macromolecular substances. The yield strength on its part is a material parameter which indicates the minimum shear stress that must be applied so that the material flows. Rheological materials in the sense of this application are transformed from a liquid state into a solidified state where, for example, an electric voltage (electric field strength) or a magnetic force (magnetic field strength) is applied. In this case, the yield strength is raised by means of a change of the impacted manipulated variable.

With a purposeful embodiment of the invention it can be envisaged that the fixation force is continually increased from an initial fixation force to a end fixation force by means of a trans-formation of the medium from a liquid state into the solidified state. The continual increasing of the fixation force, in particular the continual increasing of the yield strength, enables a gradual "glide-in" of the displaceable component into a fixed end position. Insofar as the displaceable component in the end position performs incidental movements, which are induced by incidental movements of the actuating element for example, these are subdued and restricted piece by piece by the continual increasing of the fixation force.

An advantageous embodiment of the invention envisages that the fixation force is formed with subdued incidental movements of the displaceable component in the end position, selectively with complete prevention. In what scope incidental movements of the displaceable component in the end position are subdued, this can be set by the selection of the size of the fixation force in an application-related manner. The fixation force generally acts as a counter force to the forces acting on the displaceable component in the end position which, on their part, would lead to a displacement of the displaceable component out of the end position if the fixation force was non-existent.

A preferred further development of the invention envisages that the fixation component is coupled to the actuating element and, by means of a transformation of the medium from the liquid state into the solidified state, the actuating element is fixed-positioned. In this embodiment it can be envisaged that the movement of the actuating element for the displacement of the displaceable component is passed on by way of the fixation component to the displaceable component. In one embodiment the fixation component and the actuating element are moveable relative to one another and are joined to one another. The fixation of the displaceable component in the end position can then be achieved in such a way that, with the support of the medium in the solidified state, the fixation component and the actuating element are fixed-positioned.

With an advantageous embodiment of the invention it can be envisaged that the actuating element, after the fixation of the displaceable component in the end position, is detached from the displaceable component and the displaceable component after the detachment of the actuating element is maintained in the end position with the support of the fixation force, selectively and exclusively by means of the fixation force. With the support of the fixation force involving this embodiment a sufficient holding force can also be provided for in particular, and this holding force acts against the influence of the force of gravity on the displaceable component. In a possible embodiment, the displaceable component would otherwise move out of the end position because of the force of gravity. Due to the fact that the actuating element is separated from the displaceable component, incidental movements of the actuating element are prevented from having a negative influence on the end position of the displaceable component. With piezo setting devices it is known that the applied electric voltage can lead to a resulting movement of the actuating element because of the noise of the electric voltage. The piezo setting device can be retracted by shutting off the electric voltage.

A further development of the invention can envisage that the medium is transformed from the liquid state into the solidified state wherein, with the impact of the medium with the manipulated variable, at least one parameter selected from the following group of parameters is set: temperature, in-beamed electromagnetic waves, electric voltage and magnetic force. For example, electromagnetic waves can be beamed in as light. In particular, the frequency of the waves or the in-beamed energy can be set. A combined variation of these parameters can also be envisaged.

A preferred further development of the invention envisages that the displaceable component is moved into the end position free from a guiding formed from guide elements producing friction. Guide elements producing friction are for example guide rails which guide the component to be displaced during the moving process but, on the other hand, can lead to undesirable frictional effects and restrictions with regard to the positioning accuracy or the degrees of freedom of the displacement movement. A preferred situation is the displaceable component freely positionable in an embodiment with the support of actuating elements in two or all three spatial directions.

With a purposeful embodiment of the invention it can be envisaged that the fixation component is formed as an element of a mechanism selected from the following group of mechanisms: joint mechanism and telescope mechanism. For example, it can be envisaged that the joint mechanism be at least partially immersed in the medium and "frozen in" by means of the transformation of the medium from the liquid into the solidified state. In a similar way a telescope mechanism, with which a length change of a connection can be carried out, can be "frozen in".

An advantageous embodiment of the invention envisages that, with the displacement of the displaceable component, at least one operating function selected from the following group of operating functions is performed: displacement of a measuring sampling and displacement of a measuring probe. A wide variety of examining processes are known where a measuring probe and a measuring sampling have to be moved relative to one another, and this can be to establish a certain examination configuration before the begin of an examination or during the examination itself. The scanning probe microscope is mentioned here in particular.

Advantageous embodiments of the device for the positioning of a displaceable component in an examining system are described as follows in greater detail. Embodiments and advantages result for the embodiment forms of the device according to the relevant method variants.

A preferred further development of the invention envisages that the medium is a medium corresponding to a material type selected from the following group of material types: rheological material such as electro-rheological material or magnetic-rheological material and Bingham-body.

With a purposeful embodiment of the invention it can be envisaged that the fixation device is configured in order to continually increase the fixation force from an initial fixation force to a end fixation force by means of a transformation of the medium from a liquid state into the solidified state.

An advantageous embodiment of the invention envisages that the fixation device is configured to form the fixation force subduing incidental movements of the displaceable component in the end position, selectively with complete prevention.

A further development of the invention preferably envisages that the fixation component is coupled to the actuating element which is fixation-capable by means of the transformation of the medium from the liquid state into the solidified state.

With an advantageous embodiment of the invention it can be envisaged that the actuating element after the fixation of the displaceable component in the end position is detachable from the displaceable component and the displaceable component after the detaching of the actuating element can be held stabilised in the end position with the support of the fixation force, selectively and exclusively by means of the fixation force. An alternative embodiment which can also be envisaged in one model as a type of preliminary stage for detaching the actuating element from the displaceable component is that the actuating element after the fixation is no longer impacted with the drive force. It is more so the case that this is shut off. In the case of an electric drive, this means for example that the electric drive voltage is switched off. Despite the shutoff of the drive force, the actuating element can then remain joined to the displaceable component, for example in the case of a solid coupling between the actuating element and the displaceable component.

A further development of the invention can envisage that the control device is configured so that, with the impact-application of the medium with the manipulated variable, at least one parameter selected from the following group of parameters is set: temperature, in-beamed electromagnetic waves, electric voltage and magnetic force.

A preferred further development of the invention envisages that the displaceable component can be moved into the end position free from a guiding formed from guide elements producing friction.

With a purposeful embodiment of the invention it can be envisaged that the fixation component is formed as an element of a mechanism selected from the following group of mechanisms: joint mechanism and telescope mechanism.

An advantageous embodiment of the invention envisages that the displaceable component is executed as a functional component selected from the following group of functional components: measurement sampler and measure probe.

A preferable further development of the invention envisages that the actuating element is coupled to a piezo-electrically driven setting element, selectively formed from this.

It can be envisaged that a device for the positioning of a displaceable component in one of the previously described types is arranged itself on a further displaceable component which then, on its part, is displaced according to the above-mentioned types relative to a fixed-positioned component. Such an arrangement originates, for example, when two x-y-z scanning devices, known also as scanners, are combined with one another. In this way, for example, faster scanning movements can be performed even if only smaller scanning ranges can be covered. Subsequently, positioning devices can be combined with one another wherein a positioning device takes over a rough setting and a further positioning device combined with this then takes over the precision setting. Both positioning devices, for themselves as such, are configured according to one of the previously described model types.

A DESCRIPTION OF PREFERRED
EMBODIMENT EXAMPLES OF THE
INVENTION

Figure 1B:
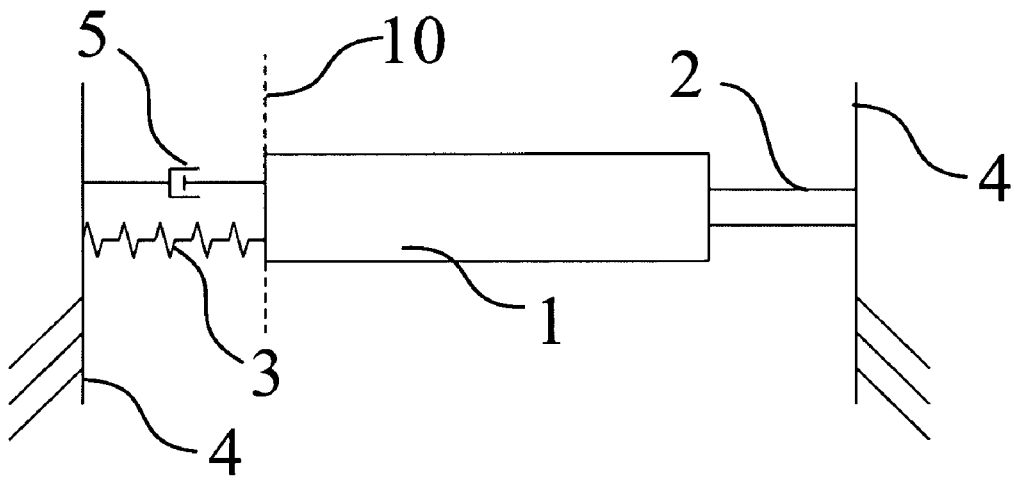
Figure 1C:
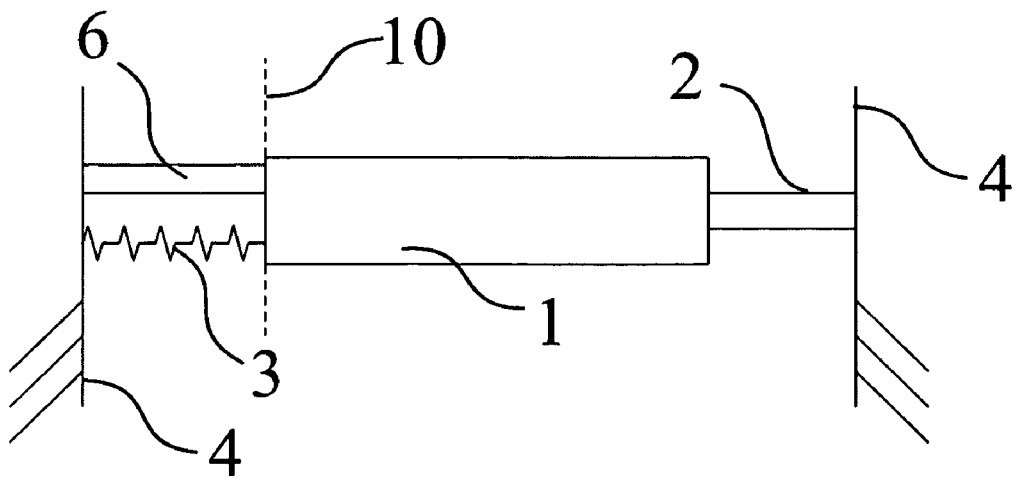
Figure 2A:
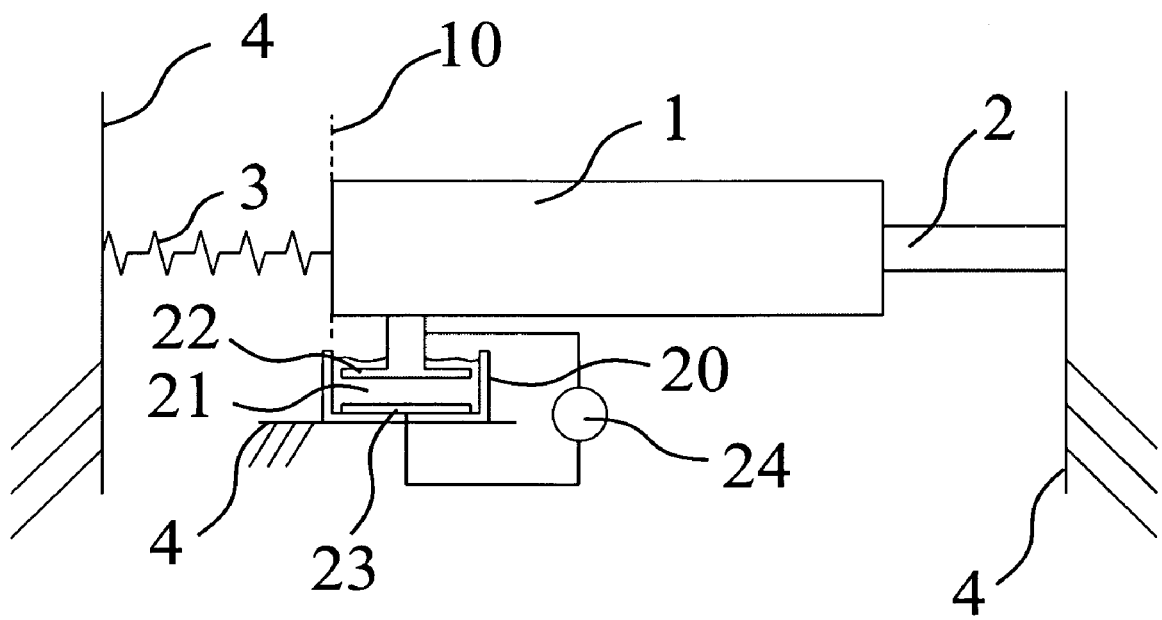
Figure 2B:
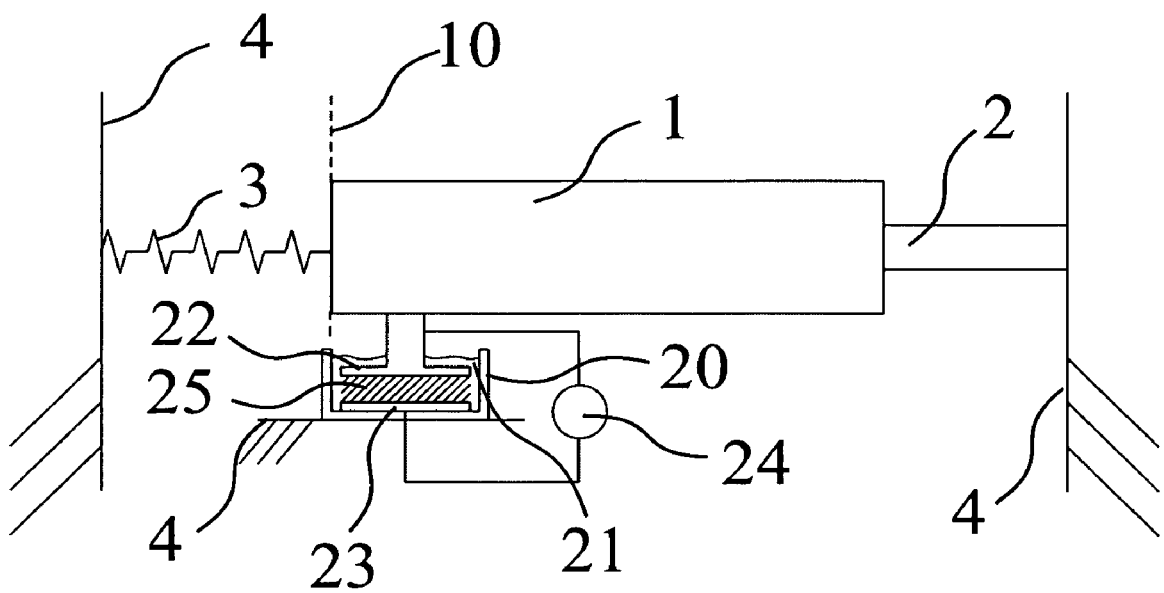
Figure 3:
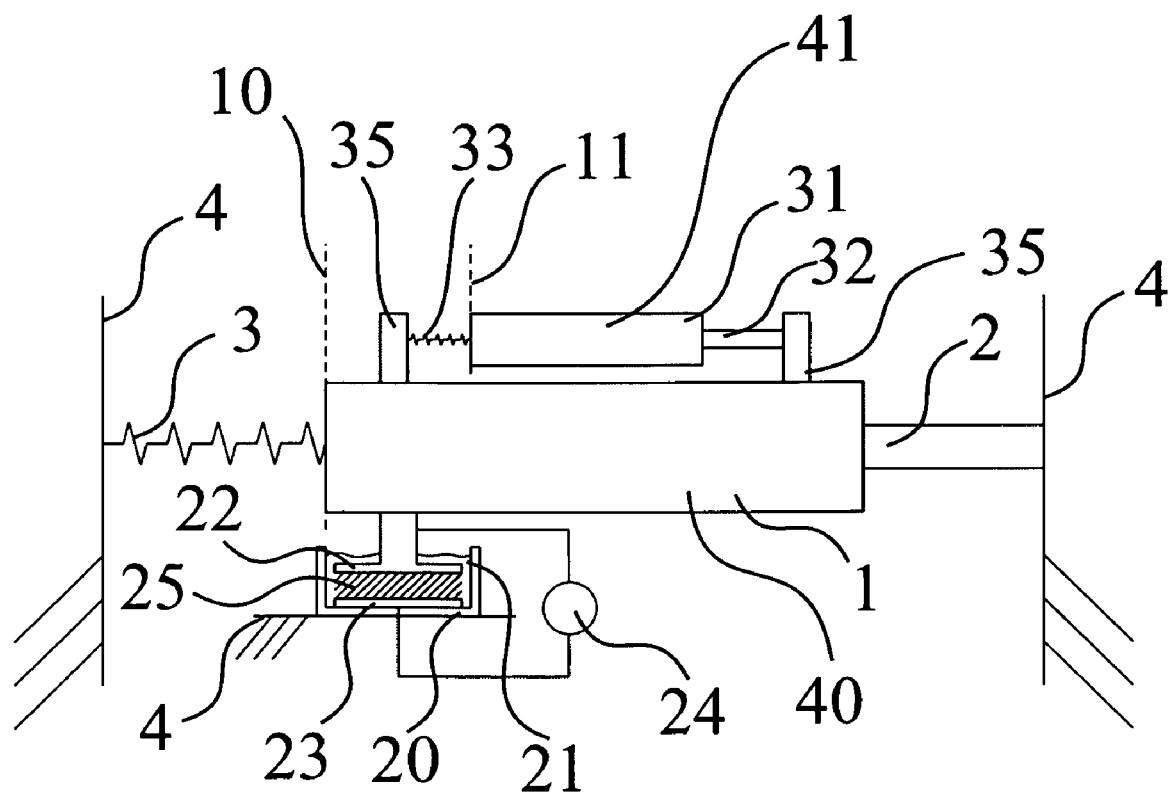

The invention is described as follows in greater detail on the basis of embodiment examples with reference to the Figures of a drawing. These Figures show the following:

FIG. 1a to 1c a schematic illustration of an arrangement with a frame and, relative thereto, a displaceable component in one embodiment;

FIGS. 2a and 2b a schematic illustration of an arrangement with a frame and, relative thereto, a displaceable component in a further embodiment; and FIG. 3 a schematic illustration of an arrangement with a frame and, relative thereto, a displaceable component on which a further positioning device is formed.

FIGS. 1a to 1b show a schematic illustration of an arrangement with a frame and, relative thereto, a displaceable component in one embodiment.

According to FIG. 1a, a displaceable component 1 is connected to a stationary formed frame 4 by way of an actuating element 2 and a spring 3. The spring 3 can also be omitted in another embodiment (not shown). The displaceable component 1 can then be screwed or glued to the actuating element 2.

According to FIG. 1b, and by means of a fixation device 5 in a desired end position, a reversible damping or movement check is introduced which can be variably controlled in terms of time.

According to FIG. 1c a fixation connection 6 is formed between the displaceable component 1 and the frame 4 with the support of the fixation devices 5. Incidental movement jolts which can be caused for example by the actuating element 2 are prevented with the support of the fixation connection 6. The reactions of the actuating element 2 and the spring 3 are then no longer significant. The transition of the fixation devices 5 into the fixation connection 6 is designed in such a way that the influence of the fixation force continually increases with the support of the fixation devices 5 and, as a result thereof, the influence of the actuating element 2 continually declines. In this way, stressing is avoided between the displaceable component 1 and the frame 4 which could otherwise lead to a displacement of the displaceable component 1 out of an end position 10.

FIGS. 1a to 1c show a one-dimensional displacement. In an analogous manner displacements of the displaceable component 1 can be envisaged wherein a positioning change takes place in more than one spatial dimension, for example in one plane. The number of the fixation connections does then not necessarily have to coincide with the number of the axes to be secured or degrees of freedom.

FIGS. 2a and 2b show a schematic illustration of an arrangement with a frame and, relative to this, a displaceable component in a further embodiment.

The fixation devices 5 envisaged for this arrangement according to the FIGS. 1a to 1c and the fixation connection 6 are replaced by a Bingham body in the form of an electro-rheological liquid. According to FIG. 2a, an electro-rheological liquid is kept in a vessel 20. Into this vessel 20, two electrodes 22, 23 submerge which are connected to a voltage source 24. Depending on the voltage placed at the two electrodes 22, 23 with the support of the voltage source 24, a stiffening in the electro-rheological liquid 21 is induced which, according to FIG. 2, ultimately leads to the formation of a fixation connection 25. The vessel 20 is solidly connected to the frame 4.

FIG. 3 shows a schematic illustration of an arrangement with a frame and, relative to this, a displaceable component on which a further positioning device is formed. For the same features, the same reference numbers are used in FIG. 3 as in the preceding Figures.

Two positioning devices, which are scanners in the illustrated embodiment example, are deployed. A lower scanner 40 can be displaced according to the previously described method and then fixed-positioned, through which the end position 10 relative to the frame 4 is defined. An upper scanner 41 with a component 31 to be moved, a setting element 32 and a spring 33 is coupled by way of structural elements 35 to a displaceable component 1 of the lower scanner 40. In this way, the upper scanner 41 can move around a middle position 11, and the end position 10 is neither changed nor disturbed in the process.

In FIG. 3, only one axis is entered in the drawing for the purpose of simplification. However, the fixation of an x-y-scanner 1, 2, 3 and the operation of a fast x-y-z-scanner with minor deflection 31, 32, 33 can also be envisaged.

An advantage of the embodiment lies in the fact that the end position 10 can be set with great precision opposite the frame 4, and with this also the end position 11. In this way, the advantages of the non-fixation-capable scanner can be utilised, such as for example high scanning speed, without the fixed-positioned scanner disturbing the movement. On the other hand, the advantages of the fixation-capable scanner, such as for example a large scanning range, can be utilised.

The features of the invention as disclosed in this description, in the claims and in the drawings can be of significance both individually and in random combination for the realisation of the invention in its various embodiments.

The invention claimed is:

1. A method for the positioning of a displaceable component in an examining system, particularly a measuring or an analytic system, where:
   the displaceable component is displaced out of a home position into an end position with the support of an actuating element coupled to the displaceable component, wherein the actuating element moved by means of a drive force, and
   the displaceable component, by way of a fixation component connected to the displaceable component, is impacted with a fixation force fixating the displaceable component in the end position, wherein the fixation component is at least partially immersed in a reservoir of a medium and is fixed-positioned in the medium by means of a transformation of the medium from a liquid state into a solidified state wherein the medium, by means of the impact-application with a manipulated variable, is transformed from the liquid state into the solidified state.

2. The method according to claim 1, wherein as a medium, a medium of at least one material type correspondingly selected from the following group of material types is adopted: rheological material such as electro-rheological material or magnetic-rheological material and Bingham-body.

3. The method according to claim 1, wherein the fixation force is continually increased by means of the transformation of the medium from the liquid state into the solidified state from an initial fixation force to and end fixation force.

4. The method according to claim 1, wherein the fixation device is configured to form the fixation force subduing incidental movements of the displaceable component in the end position, selectively with complete prevention.

5. The method according to claim 1, wherein the fixation component is coupled to the actuating element and the actuating element fixed-positioned by means of the transformation of the medium from the liquid state into the solidified state.

6. The method according to claim 1, wherein the actuating element, after the fixation of the displaceable component in the end position, is detached from the displaceable component and the displaceable component after the detachment of the actuating element is maintained in the end position with the support of the fixation force, selectively and exclusively by means of the fixation force.

7. The method according to claim 1, wherein the medium is transformed from the liquid state into the solidified state wherein, with the impact of the medium with the manipulated variable, at least one parameter selected from the following group of parameters is set: temperature, in-beamed electromagnetic waves, electric voltage and magnetic force.

8. The method according to claim 1, wherein the displaceable component is moved into the end position free from a guiding formed from guide elements producing friction.

9. The method according to claim 1, wherein the fixation component is formed as an element of a mechanism selected from the following group of mechanisms: joint mechanism and telescope mechanism.

10. The method according to claim 1, wherein with the displacement of the displaceable component, at least one operating function selected from the following group of operating functions is performed: displacement of a measuring sampling and displacement of a measuring probe.

11. A device for the positioning of a displaceable component in an examining system, particularly a measuring or an analytic system, with:
    a displaceable component,
    an actuating element coupled to the displaceable component, where this actuating element is moveable in order to displace the displaceable component out of a home position into an end position, and
    a fixation device with:
    a fixation component which is connected to the displaceable component,
    a reservoir of a medium in which the fixation component can be at least partially submerged, and
    a control device which is configured for impacting the medium with a manipulated variable in order to transform the medium between a liquid state and a solidified state, selectively all the way up to a solid body characterisation.

12. The device according to claim 11, wherein the medium is a medium of at least one material type correspondingly selected from the following group of material types: rheological material such as electro-rheological material or magnetic-rheological material and Bingham-body.

13. The device according to claim 11, wherein the fixation device is configured in order to continually increase the fixation force by means of a transformation of the medium from the liquid state into the solidified state from an initial fixation force to an end fixation force.

14. The device according to claim 11, wherein the fixation device is configured to form the fixation force subduing incidental movements of the displaceable component in the end position, selectively with complete prevention.

15. The device according to claim 11, wherein the fixation component is coupled to the actuating element and the actuating element can be fixed-positioned by means of the transformation of the medium from the liquid state into the solidified state.

16. The device method according to claim 11, wherein the actuating element, after the fixation of the displaceable component in the end position, can be detached from the displaceable component and the displaceable component after the detachment of the actuating element can be maintained in the end position with the support of the fixation force, selectively and exclusively by means of the fixation force.

17. The device according to claim 11, wherein the control device is configured, with the impact of the medium with the manipulated variable, to set at least one parameter selected from the following group of parameters: temperature, in-beamed electromagnetic waves, electric voltage and magnetic force.

18. The device according to claim 11, wherein the displaceable component can be moved into the end position free from a guiding formed from guide elements producing friction.

19. The device according to claim 11, wherein the fixation component is formed as an element of a mechanism selected from the following group of mechanisms: joint mechanism and telescope mechanism.

20. The device according to claim 11, wherein the displaceable component is executed as a functional component selected from the following group of functional components: measuring sampling and measuring probe.

21. The device according to claim 11, wherein the actuating element is coupled to a piezo-electrically operated setting element.

* * * * *